(12) United States Patent
Brogan

(10) Patent No.: US 7,306,785 B2
(45) Date of Patent: Dec. 11, 2007

(54) MULTIFUNCTIONAL CROSS-BRIDGED TETRAAZA MACROCYCLIC COMPOUNDS AND METHODS OF MAKING AND USING

(75) Inventor: John Bucknam Brogan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 457 days.

(21) Appl. No.: 10/947,112

(22) Filed: Sep. 23, 2004

(65) Prior Publication Data

US 2006/0062728 A1    Mar. 23, 2006

(51) Int. Cl.
*A61B 5/055* (2006.01)

(52) U.S. Cl. ............... 424/9.363; 424/1.11; 424/1.65; 424/1.81; 424/9.3; 424/9.362; 424/9.4

(58) Field of Classification Search ............... 424/1.11, 424/1.65, 9.1, 9.2, 9.3, 9.4, 9.5, 9.6, 9.7, 424/9.8, 9.362, 1.53, 9.363, 9.364, 1.81; 534/7, 10–16; 540/450
See application file for complete search history.

(56) References Cited

U.S. PATENT DOCUMENTS

| | | | |
|---|---|---|---|
| 4,361,544 A | 11/1982 | Goldenberg | |
| 4,474,893 A | 10/1984 | Reading | |
| 4,479,895 A | 10/1984 | Auditore-Hargreaves | |
| 4,946,778 A | 8/1990 | Ladner et al. | |
| 6,395,474 B1 | 5/2002 | Buchardt et al. | |
| 6,451,968 B1 | 9/2002 | Egholm et al. | |
| 6,489,472 B2 | 12/2002 | Giandomenico et al. | |
| 6,555,681 B1 | 4/2003 | Hiler, II et al. | |
| 6,656,450 B2 | 12/2003 | Hubin et al. | |

OTHER PUBLICATIONS

Golub et al., Science, vol. 286, Oct. 15, 1999, pp. 531-537.*
X. Sun et al., "Radiolabeling and In Vivo Behavior of Copper-64-Labeled Crosss-Bridged Cyclam Ligands," J. Med. Chem., vol. 45, pp. 469-477 (2002).
E.H. Wong et al., J. Am. Chem. Soc., vol. 122, pp. 10561-10572 (2000).
W.J. Krupper et al., J. Org. Chem., vol. 58, pp. 3869-3876 (1993).
Milstein et al., Immunology Today, vol. 5, (1984), 299-304.
L.L. Chappell et al., "Improved Synthesis of the Bifunctional Chelating Agent 1,4,7,10-Tetraaza-N-(1-carboxy-3-(4-nitrophenyl)-N',N'',N'''-tris(acetic acid)cyclododecane," Bioorg. Med. Chem., vol. 7, No. 11, 2313-20 (1999).

* cited by examiner

*Primary Examiner*—Dameron L. Jones
(74) *Attorney, Agent, or Firm*—Maureen Bresnahan; Jean K. Testa

(57) ABSTRACT

A multifunctional cross-bridged tetraaza macrocyclic compound has at least one side arm that comprises a moiety that is capable of forming a bond with another molecule, which has a targeting moiety that directs the compound to a site a marker substance. The compound is chelated to a medically active material that generates a signal for diagnostic imaging or produces a therapeutic effect at the site of the marker substance. A method for detecting, diagnosing, and/or treating a disease that produces the marker substance uses a conjugate comprising the multifunctional cross-bridged tetraaza macrocyclic compound.

6 Claims, No Drawings

MULTIFUNCTIONAL CROSS-BRIDGED TETRAAZA MACROCYCLIC COMPOUNDS AND METHODS OF MAKING AND USING

The present invention relates to multifunctional cross-bridged tetraaza macrocyclic compounds. Further, the present invention relates to applications of such compounds in the medical diagnostic and therapeutic fields.

BACKGROUND OF THE INVENTION

The growing need for the early diagnosis and assessment and/or treatment of diseases can potentially be addressed by pharmaceuticals that preferentially accumulate at the disease sites. In diagnostic applications, these pharmaceuticals can elucidate the state of the disease through its distinctive molecular biology expressed as disease markers that are not present, or are present in diminished levels, in healthy tissues. In therapeutic applications, these pharmaceuticals can deliver an enhanced dose of therapeutic agents to the disease sites through specific interactions with the disease markers. By specifically targeting physiological or cellular functions that are present only in disease states, these pharmaceuticals can report exclusively on the scope and progress of that disease or exclusively target the diseased tissue. A signal-generating or signal-enhancing moiety is a key element of these diagnostic pharmaceuticals, which produce differentiated signals at the disease sites. Such signals can be captured and processed to produce images of the tissue of interest. Many such signal-generating or signal-enhancing moieties comprise metals, which are often physiologically toxic in their uncombined forms. Therefore, these metals are often bound to chelators to form nontoxic complexes. The utility of such a diagnostic pharmaceutical is much enhanced if the metal is not easily dissociated from the chelator moiety before the complex reaches the disease site. Furthermore, such a diagnostic pharmaceutical should be provided with a moiety that targets the disease sites.

To date, a number of chelators have been used, including diethylenetriaminepentaacetic acid ("DTPA"); 1,4,7,10-tetraazacyclododecane'-N,N'N",N'''-tetracetic acid ("DOTA"); and derivatives thereof. These chelators have acceptably high stability constants (also known as formation constants) with respect to gadolinium, and thus could act to detoxify gadolinium ions. However, the stability constant of a chelator with respect to useful metals or metal ions varies. Therefore, a continued need exists for chelators that have high stability constants with respect to many useful metals or metals ions that may be used in designing many diagnostic pharmaceuticals. It is also desirable to provide metal-chelator complexes that are readily conjugatable to molecules that can accumulate at disease sites.

SUMMARY OF THE INVENTION

The present invention provides multifunctional macrocyclic compounds that can form complexes with metals or metal ions. In general, a multifunctional macrocyclic compound of the present invention has a formula:

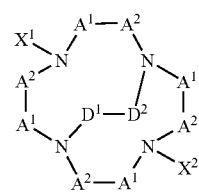

(I)

wherein each -A$^1$-A$^2$- is a group independently selected from the group consisting of —CR$_2$—CR$_2$—, —CR=CR—, CR$_2$—CR$_2$—CR$_2$—, —CR=CR—CR$_2$—, and —CR$_2$—CR=CR—; X$^1$ and X$^2$ are independently selected from the group consisting of —(CR$_2$)$_n$—COO$^-$, —(CR$_2$)$_n$—COOH, —CR((CR$_2$)$_m$—COO$^-$)$_2$, —CR—((CR$_2$)$_m$—COOH)$_2$, —(CR$_2$)$_n$—CR—((CR$_2$)$_m$—COO$^-$)$_2$, and —(CR$_2$)$_n$—CR—((CR$_2$)$_m$—COOH)$_2$, wherein each of n and m is an independently selected integer such that $1 \leq n \leq 5$, and $0 \leq m \leq 5$; -D$^1$-D$^2$- is selected from the group consisting of —CR$_2$—CR$_2$— and —CR=CR—; and each R is independently selected from the group consisting of hydrogen, unsubstituted or substituted alkyl groups, unsubstituted or substituted alkoxy groups, unsubstituted or substituted aryl groups, unsubstituted or substituted alkylaryl groups, unsubstituted or substituted heterocyclic groups, alcohol, amino, amido, nitro, ether, ester, keto, imino, aldehyde, carbonyl, halogen-containing moieties, sulfur-containing moieties, phosphorus-containing moieties, and derivatives thereof.

In one aspect, the multifunctional macrocyclic compound forms a complex with a metal.

In another aspect, a multifunctional macrocyclic compound of the present invention also has a moiety that forms a bond with another molecule.

In still another aspect, a multifunctional macrocyclic compound has a formula:

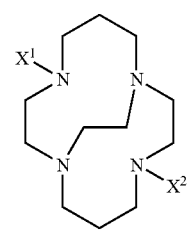

(II)

wherein at least one of X$^1$ and X$^2$ comprises a carboxylic acid group, and at least one of X$^1$ and X$^2$ comprises a terminal isothiocyanate moiety.

Other features and advantages of the present invention will be apparent from a perusal of the following detailed description of the invention and the accompanying drawings in which the same numerals refer to like elements.

DETAILED DESCRIPTION OF THE INVENTION

The present invention provides multifunctional macrocyclic compound that can form complexes with metals or metal ions. Embodiments of the complexes of the present invention can be used as diagnostic imaging or therapeutic agents. In general, a multifunctional macrocyclic compound of the present invention has a formula:

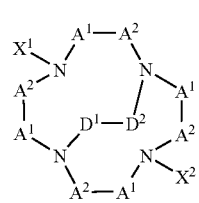

(I)

wherein each -A$^1$-A$^2$- is a group independently selected from the group consisting of —CR$_2$—CR$_2$—, —CR=CR—, CR$_2$—CR$_2$—CR$_2$—, —CR=CR—CR$_2$—, and —CR$_2$—CR═CR—; X$^1$ and X$^2$ are independently selected from the group consisting of —(CR$_2$)$_n$—COO$^-$, —(CR$_2$)$_n$—COOH, —CR((CR$_2$)$_m$—COO$^-$)$_2$, —CR—((CR$_2$)$_m$—COOH)$_2$, —(CR$_2$)$_n$—CR—((CR$_2$)$_m$—COO$^-$)$_2$, and —(CR$_2$)$_n$—CR—((CR$_2$)$_m$—COOH)$_2$, wherein each of n and m is independently selected integers such that $1 \leq n \leq 5$, and $0 \leq m \leq 5$; -D$^1$-D$^2$- is selected from the group consisting of —CR$_2$—CR$_2$— and —CR═CR—; and each R is independently selected from the group consisting of hydrogen, unsubstituted or substituted alkyl groups, unsubstituted or substituted alkoxy groups, unsubstituted or substituted aryl groups, unsubstituted or substituted alkylaryl groups, unsubstituted or substituted heterocyclic groups, alcohol, amino, amido, nitro, ether, ester, keto, imino, aldehyde, carbonyl, halogen-containing moieties, sulfur-containing moieties, phosphorus-containing moieties, and derivatives thereof.

In one aspect of the present invention, at least one of X$^1$ and X$^2$ comprises a moiety that is capable of forming a bond with another molecule. Such a moiety is termed herein a "linking moiety." Preferably, such a bond is a covalent bond. The resulting compound is hereinafter termed a "multifunctional conjugate." In certain embodiments of the present invention, the linking moiety is selected from the group consisting of isocyanate group and isothiocyanate group.

In certain embodiments of the present invention, the metal or metal ion is bound sufficiently strongly to the macrocyclic compound (i.e., the resulting complex is sufficiently stable) at physiologically relevant conditions. Therefore, the inherent toxicity of the free metal or metal ion is greatly reduced.

The term "alkyl," as used herein, means a straight or branched chain alkyl group, with straight chain alkyl groups being preferred. If branched, it may be branched at one or more positions, and unless specified, at any position. Also included within the definition of "alkyl" are heteroalkyl groups, wherein the heteroatom is selected from the group consisting of nitrogen, oxygen, phosphorus, sulfur, and silicon. The alkyl group may range from about 1 to 20 carbon atoms (C$_1$-C$_{20}$), with a preferred embodiment utilizing from about 1 to about 10 carbon atoms (C$_1$-C$_{10}$), with about C$_1$ through about C$_5$ being more preferred. However, in some embodiments, advantages may be realized with larger alkyl groups. Also included within the definition of an alkyl group are cycloalkyl groups such as rings having 5 or 6 carbon atoms, and heterocycloalkyl.

The term "aryl," as used herein, means a group comprising at least one aromatic ring, which may be unsubstituted or substituted, such as phenyl, benzyl, biphenyl, terphenyl, pyridine, and groups comprising fused rings (such as naphthyl, or groups derived from anthracene, phenanthrene, or fluorene).

Suitable substitution groups for substituted alkyl and aryl groups include, but are not limited to, halogens such as chlorine, bromine and fluorine, amines, hydroxy group, carboxylic acid group, nitro group, carbonyl, and other alkyl and aryl groups as defined herein. Thus, arylalkyl and hydroxyalkyl groups are also suitable for use in the invention.

The term "heterocyclic," as used herein, means a group comprising at least one ring, wherein at least a heteroatom occupies a ring position, such as furan, thiophene, pyrrole, indole, purines, pyrimidines, and derivatives thereof. Such a heteroatom may be selected from the group consisting of nitrogen, oxygen, sulfur, and phosphorus.

In another aspect, a multifunctional macrocyclic compound of the present invention has a formula:

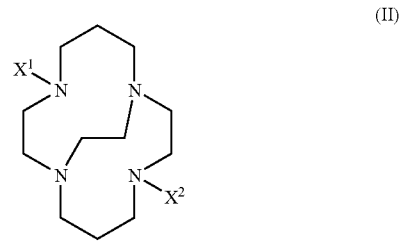

(II)

wherein at least one of X$^1$ and X$^2$ comprises a carboxylic acid group, and at least one of X$^1$ and X$^2$ comprises a linking moiety that can readily form a bond with another organic compound such as a peptide, a protein, or a derivative thereof. Preferably, such a bond is a covalent bond.

In one embodiment, the linking moiety is the isothiocyanate moiety that can form a disulfide bond with a cysteine residue in a protein, or a fragment thereof.

In another embodiment, the linking moiety is the carboxylic acid group that can form an amide bond with a side amino group; for example, of a lysine residue in a protein, or a fragment thereof.

In still another embodiment, the linking moiety is an amino group that can form an amide bond with a side carboxylic acid group; for example, of a glutamic acid or an aspartic acid residue in a protein, or a fragment thereof.

In one embodiment, a multifunctional macrocyclic compound has a formula of:

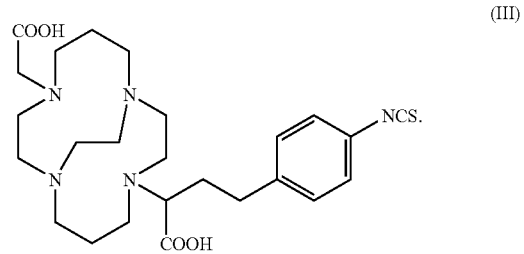

(III)

In another embodiment, a multifunctional macrocyclic compound has a formula of:

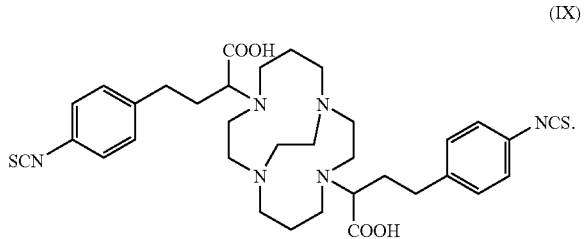

(IX)

In still other embodiments, one or both of the isothiocyanate moieties in formulas (III) and (IX) are replaced by isocyanate, amido, or carboxylic group.

Compound III was synthesized according to the synthesis scheme below and is disclosed in the following procedure. All reagents were purchased without further purification. Reactions were carried out under inert atmosphere and monitored by TLC column chromatography was conducted using silica gel 60 (230×400 mesh, or size range from about 37 micrometers to about 63 micrometers).

(Equation 1)

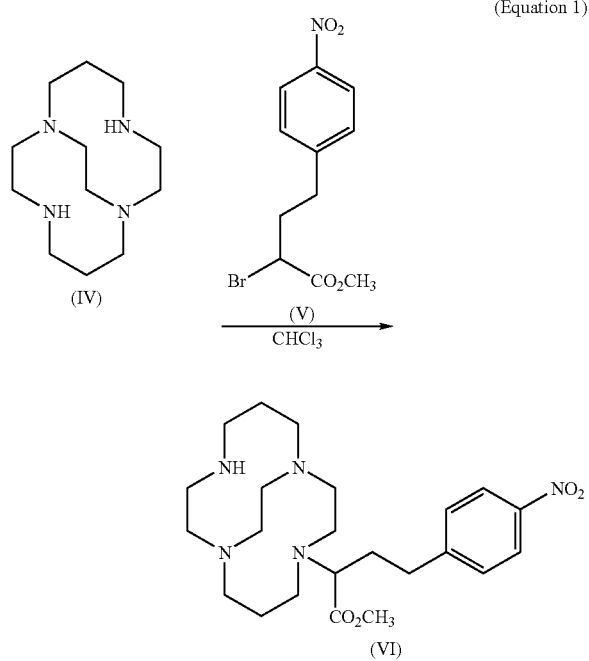

(Equation 2)

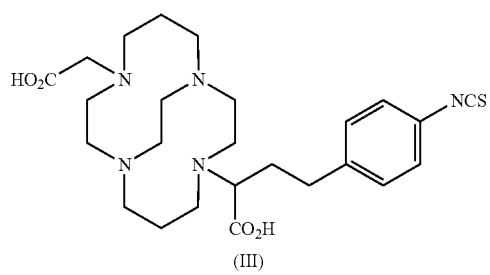

(Equation 3)

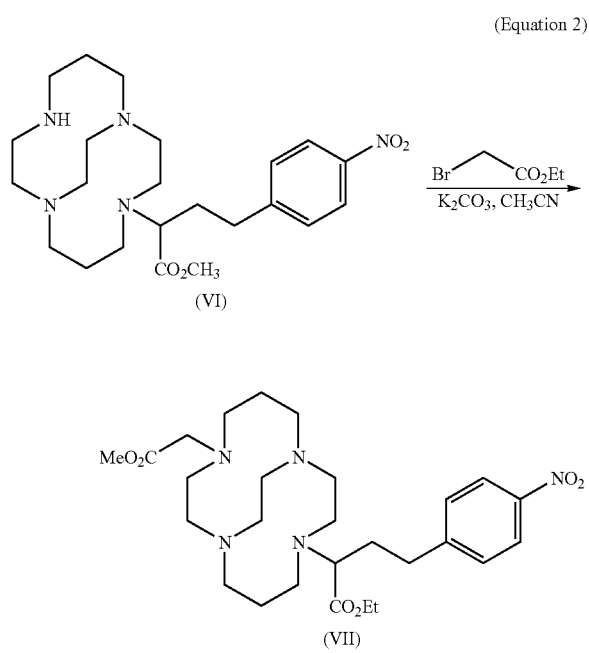

-continued (III)

Monoester (VI) was first synthesized as follows. A solution of tetraamine (IV) (589 mg, 2.5 mmol) (E. H. Wong et al., J. Am. Chem. Soc., Vol. 122, pp. 10561-10572 (2000)) in chloroform (100 ml) was treated with bromide (V) (627 mg, 2.1 mmol) (W. J. Krupper et al., J. Org. Chem., Vol. 58, pp. 3869-3876 (1993)) and stirred for 24 h. The solution was concentrated and the residue was chromatographed on silica to provide the mono alkylation product (VI) as the major component (130 mg, 11%). ESI-MS (M+H)=448.

A solution of monoester (VI) (130 mg, 0.29 mmol) dissolved in acetonitrile (2 ml) was treated with $K_2CO_3$ (40 mg, 0.29 mmol) and ethyl bromoacetate (32 ml, 0.29 mmol). The mixture was heated at 50 C for 24 h to concentrate. The residue was chromatographed on silica to provide the diester (VII). The yield was not determined. ESI-MS (M+H)=534.

Monoester (VI) or diester (VII) can be converted to compound (III) of the present invention by following the method disclosed in L. L. Chappell et al., "Improved Synthesis of the Bifunctional Chelating Agent 1,4,7,10-Tetraaza-N-(1-carboxy-3-(4-nitrophenyl)-N',N'',N'''-tris(acetic acid)cyclodecane," Bioorg. Med. Chem., Vol. 7, No. 11, 2313-20 (1999). For example, the ester groups in monoester VI or diester VII can be converted to carboxylic acid group by refluxing with concentrated hydrochloric acid. The nitro group is converted to an amine group by hydrogenation using a Pd-loaded carbon catalyst. The resulting amine group is converted to the isothiocyanate group by reacting with SCCl2 in CHCl3. The reactions can be carried out at room temperature or an elevated temperature.

Various metals or metals ions can be chelated to a multifunctional macrocyclic compound of the present invention. These metals or their ions, for example radionuclides, can serve diagnostic imaging or therapeutic purposes. Suitable radioisotopes or their ions include actinium-225, bismuth-212, arsenic-72, indium-110, indium-111, indium-113m, gallium-67, gallium-68, strontium-83, zirconium-89, ruthenium-95, ruthenium-97, ruthenium-103, ruthenium-105, mercury-107, mercury-203, rhenium-186, rhenium-188, tellurium-121m, tellurium-122m, tellurium-125m, thulium-165, thulium-167, thulium-168, technetium-94m, technetium-99m, silver-111, platinum-197, palladium-109, copper-62, copper-64, copper-67, yttrium-86, yttrium-90, scandium-47, samarium-153, lutetium-177, rhodium-105, praseodymium-142, praseodymium-143, terbium-161, holmium-166, gold-199, cobalt-57, cobalt-58, chromium-51, iron-59, selenium-75, thallium-201, and ytterbium-169. Preferably, the radioisotope will emit a particle or ray in the 10-7,000 keV range, more preferably 50-1,500 keV.

Isotopes preferred for imaging applications include indium-111, gallium-67, ruthenium-97, technetium-99m, cobalt-57, cobalt-58, chromium-51, iron-59, selenium-75, thallium-201, ytterbium-169, and copper-64.

Isotopes preferred for therapeutic use include actinium-225, bismuth-212, lead-212, bismuth-213, rhenium-186, rhenium-188, silver-111, platinum-197, palladium-109, copper-67, copper-64, yttrium-90, scandium-47, samarium-153, lutetium-177, rhodium-105, praseodymium-142, praseodymium-143, terbium-161, holmium-166, and gold-199.

A multifunctional macrocyclic compound of the present invention is advantageously linked, for example through a covalent bond, to another molecule via the linking moiety in one of $X^1$ and $X^2$. When both $X^1$ and $X^2$ comprise linking moieties, the multifunctional macrocyclic compound can be linked to at least two other molecules of the same or different types. For example, when such other molecules preferentially accumulate at or target, a disease site, a complex of the present invention carrying the diagnostic imaging or therapeutic agent can be targeted to such disease site. In these embodiments, each of such other molecules comprises at least a targeting moiety that binds a marker substance that is produced by or associated with the diseased tissue. The term "targeting moiety," as used herein, means a functional group, which serves to target or direct the complex to a particular location, cell type, diseased tissue, or association. In general, the targeting moiety is directed against a target molecule or a portion thereof. A complex comprising a multifunctional conjugate and a diagnostic imaging or therapeutic agent of the present invention can be injected intravenously; thus preferred targeting moieties are those that allow concentration of the agent in a particular localization for which the agent is intended. Thus, for example, antibodies, cell surface receptor ligands and hormones, lipids, sugars and dextrans, alcohols, bile acids, fatty acids, amino acids, peptides, nucleic acids, and derivatives thereof may all be attached to localize or target the agent to a particular site. In one embodiment, the marker substance is a native marker substance; i.e., that is over-produced or over-expressed naturally by the diseased tissue. In another embodiment, the marker substance can be a bispecific compound that has a first moiety that binds to a native marker substance and a second moiety that binds to the targeting moiety. In this case, the second moiety of the marker substance and the targeting moiety of the complex diagnostic imaging or therapeutic agent can comprise a complementary binding pair, such as a DNA sequence and its complementary sequence or a peptide nucleic acid ("PNA") sequence and its complementary sequence. PNAs are disclosed, for example, in U.S. Pat. Nos. 6,395,474 and 6,451,968.

In an embodiment, the compound that comprises the targeting moiety and is linked to the multifunctional macrocyclic compound is an antibody or an antibody fragment. The terms "antibodies" and "antibody fragments" mean generally immunoglobulins or fragments thereof that specifically bind to antigens to form immune complexes.

The antibody may be a whole immunoglobulin of any class; e.g., IgG, IgM, IgA, IgD, IgE, chimeric or hybrid antibodies with dual or multiple antigen or epitope specificities. It can be a polyclonal antibody, preferably an affinity-purified antibody from a human. It can be an antibody from an appropriate animal; e.g., a primate, goat, rabbit, mouse, or the like. If the target site-binding region is obtained from a non-human species, it is preferred that the target species is humanized to reduce immunogenicity of the non-human antibodies, for use in human diagnostic or therapeutic applications. Such a humanized antibody or fragment thereof is also termed "chimeric." For example, a chimeric antibody comprises non-human (such as murine) variable regions and human constant regions. A chimeric antibody fragment can comprise a variable binding sequence or complementary-determining regions ("CDR") derived from a non-human antibody within a human variable region framework domain. Monoclonal antibodies are also suitable for use in the present invention, and are preferred because of their high specificities. They are readily prepared by what are now considered conventional procedures of immunization of mammals with an immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility in the present invention. It will be appreciated that newer techniques for production of monoclonal antibodies ("MAb") can also be used; e.g., human MAbs, interspecies MAbs, chimeric (e.g., human/mouse) MAbs, genetically engineered antibodies, and the like.

Antibody fragments useful in the present invention include F(ab')$_2$, F(ab)$_2$, Fab', Fab, Fv, and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. An antibody fragment can include genetically engineered and/or recombinant proteins, whether single-chain or multiple-chain, which incorporate an antigen-binding site and otherwise function in vivo as targeting species in substantially the same way as natural immunoglobulin fragments. Such single-chain binding molecules are disclosed in U.S. Pat. No. 4,946,778. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin. The fragments may also be produced by genetic engineering.

It should be noted that mixtures of antibodies and immunoglobulin classes can be used, as can hybrid antibodies. Multispecific, including bispecific and hybrid, antibodies and antibody fragments are sometimes desirable in the present invention for detecting and treating lesions and comprise at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the targeted lesion. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in; e.g., U.S. Pat. Nos. 4,474,893 and 4,479,895, and in Milstein et al., Immunology Today, Vol. 5, 299 (1984).

In another embodiment, the targeting moiety is all or a portion (e.g. a binding portion) of a ligand for a cell surface receptor. Suitable ligands include, but are not limited to, all or a functional portion of the ligands that bind to a cell surface receptor selected from the group consisting of insulin receptor (insulin), insulin-like growth factor receptor (including both IGF-1 and IGF-2), growth hormone receptor, glucose transporters (particularly GLUT 4 receptor), transferring receptor (transferring), epidermal growth factor receptor (EGF), low density lipoprotein receptor, high density lipoprotein receptor, leptin receptor, estrogen receptor (estrogen); interleukin receptors including IL-1, IL-2, IL-3, IL-4, IL-5, IL-6, IL-7, IL-8, IL-9, IL-11, IL-12, IL-13, IL-15, and IL-17 receptors, human growth hormone receptor, vascular endothelial growth factor ("VEGF") receptor, platelet-derived growth factor ("PDGF") receptor, transforming growth factor receptor (including TGF-α and TGF-β), erythropoietin ("EPO") receptor, thrombopoietin ("TPO") receptor, ciliary neurotrophic factor receptor, prolactin receptor, and T-cell receptors. In particular, hormone ligands are preferred. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathyroid hormone, thyroid-stimulating hormone (TSH), vasopressin, enkephalins, seratonin, estradiol, progesterone, testosterone, cortisone, and glucocorticoids and the hormones listed above. Receptor ligands include ligands that bind to receptors such as cell surface receptors, which include hormones, lipids, proteins, glycoproteins, signal transducers, growth factors, cytokines, and others.

In another embodiment, the targeting moiety is a carbohydrate. The term "carbohydrate," as used herein, means a compound with the general formula $C_x(H_2O)_y$. Monosaccharides, disaccharides, and oligo- or polysaccharides are all included within the definition and comprise polymers of various sugar molecules linked via glycosidic linkages. Particularly suitable carbohydrates are those that comprise all or part of the carbohydrate component of glycosylated proteins, including monomers and oligomers of galactose, mannose, fuctose, galactamine, (particularly N-acetylglucosamine), glucosamine, glucose and sialic acid (N-acetylneuraminic acid), and in particular the glycosylation component that allows binding to certain receptors such as cell surface receptors. Other carbohydrates comprise monomers and polymers of glucose, ribose, lactose, raffinose, fructose, and other biologically significant carbohydrates.

In another embodiment, the targeting moiety is a lipid. The term "lipid," as used herein, includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol.

In another embodiment, the targeting moiety is selected from the group consisting of enzyme substrates, enzyme inhibitors, and ion binding compounds or moieties.

In still another embodiment, the targeting moiety may be used to either allow the internalization of the diagnostic imaging or therapeutic agent to the cell cytoplasm or localize it to a particular cellular compartment, such as the nucleus.

In still another embodiment, a plurality of multifunctional macrocyclic compounds of the present invention is attached via the linking moieties to a plurality of units or residues of a polymer. Suitable polymers are those that contain or can be modified to contain functional groups that form covalent bonds with the linking moieties of the plurality of multifunctional macrocyclic compounds. Non-limiting examples of suitable polymers are dextrans and polypeptides that comprise units selected from the group consisting of lysine, arginine, glutamine, asparagines, aspartic acid, glutamic acid, and combinations thereof. Particularly suitable is polylysine. In one embodiment, there is provided a polylysine having 100-600 lysine repeating units, a majority (such as 60-98 percent) of which is covalently linked to the multifunctional macrocyclic compounds of the present invention; for example, through the formation of amide bonds with the amino side groups of the lysine residues. The macrocyclic compounds are used to chelate paramagnetic ions, such as iron or gadolinium, to provide agents that can enhance the contrast of images obtained with the magnetic resonance technique.

Methods for Diagnosing or Treating Diseases Using Multifunctional Macrocyclic Compounds A multifunctional conjugate of the present invention that comprises a multifunctional macrocyclic compound chelating with a metal or metal ion and being conjugated with another molecule having a targeting moiety is used in a method for detecting, diagnosing, and/or treating a disease condition by delivering the metal or metal ion, which comprises an active agent (diagnostic, therapeutic, or both), to the site of a disease. A patient in a method of the present invention can be human or non-human. In general, the method comprises administering a multifunctional conjugate into the patient or subject. The step of administering can be carried out intravenously along with a physiologically acceptable carrier.

In one embodiment, the active agent comprises a metal or metal ion that generates a unique signal that is recognizable by diagnostic medical imaging techniques, such as MRI, PET, SPECT, or combinations thereof. The multifunctional conjugate in circulation, through its targeting moiety, seeks out and binds to the marker substance, and thus delivers the active agent to the site of the marker substance. Thereafter, an image of the portion of the body around the site of the marker substance is obtained by one or a combination of these diagnostic imaging techniques.

In another embodiment, the metal or metal ion is a radioisotope that emits radiation useful for therapy purposes.

In another embodiment, the method comprises: (a) administering a first compound that comprises a marker-substance targeting moiety and a first member of a binding pair; (b) allowing the first compound to accumulate at a site of the marker substance; and (c) administering a second compound that comprises a conjugate of: (1) a multifunctional macrocyclic compound chelated to a metal or metal ion, and (2) a second member of the binding pair that is complementary to the first member of the binding pair. Such a multifunctional macrocyclic compound and such a metal or metal ion are disclosed above.

In another embodiment, the method further comprises: (d) allowing the second compound to bind to the first compound; and (e) obtaining an image of the site of the marker substance reconstructed from the signal generated by the metal or metal ion.

In various aspects of a method of the present invention, a metal or an ion thereof can be selected among the metals disclosed herein above to suit the particular circumstances and disease.

While various embodiments are described herein, it will be appreciated from the specification that various combinations of elements, variations, equivalents, or improvements therein may be made by those skilled in the art, and are still within the scope of the invention as defined in the appended claims.

What is claimed is:

1. A multifunctional macrocyclic compound having a formula of

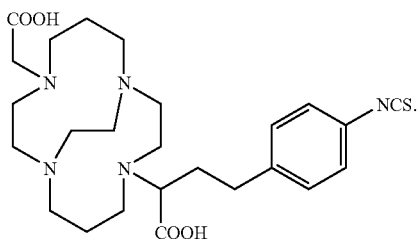

(III)

2. The multifunctional macrocyclic compound of claim 1, wherein said multifunctional macrocyclic compound is chelated to a metal or metal ion that is detectable by a technique selected from the group consisting of MRI, PET, SPECT, and combinations thereof.

3. The multifunctional macrocyclic compound of claim 1, wherein said multifunctional macrocyclic compound is chelated to copper-64.

4. A multifunctional macrocyclic compound having a formula of:

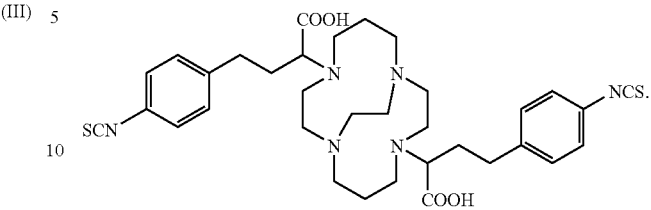

(IX)

5. The multifunctional macrocyclic compound of claim 4, wherein said multifunctional macrocyclic compound is chelated to a metal or metal ion that is detectable by a technique selected from the group consisting of MRI, PET, SPECT, and combinations thereof.

6. The multifunctional macrocyclic compound of claim 4, wherein said multifunctional macrocyclic compound is chelated to copper-64.

* * * * *